United States Patent [19]
Fujishima et al.

[11] Patent Number: 5,744,325
[45] Date of Patent: Apr. 28, 1998

[54] PROCESS FOR PRODUCING N-ACETYLGLUCOSAMINE-6-PHOSPHATE DEACETYLASE

[75] Inventors: Shizu Fujishima; Naoko Yamano, both of Ikeda; Akihiko Maruyama; Takanori Higashihara, both of Tsukuba, all of Japan

[73] Assignee: Agency of Industrial Science and Technology, Tokyo, Japan

[21] Appl. No.: 806,613

[22] Filed: Feb. 26, 1997

[30] Foreign Application Priority Data

Mar. 4, 1996 [JP] Japan .................. 8-075250

[51] Int. Cl.$^6$ .............. C12P 21/04; C12N 9/80; C12N 1/12
[52] U.S. Cl. .............. 435/71.2; 435/252.1; 435/228
[58] Field of Search .............. 435/227, 228, 435/252.1, 71.1, 71.2

[56] References Cited

PUBLICATIONS

Yamano et al. "Purification and characterization of N–acetylglucosamine–6–6phosphate deacetylase with activity against N–acetylglucosamine from *Virio cholerae* non–01", Bioscie. Biotech. Biochem. (1996) 60(8): 1320–1323.

Bouma et al. "Sugar transport by the marine chitinolytic bacterium *Vibrio furnissii*", J. Biol. Chem. (1996) 271(52): 33468–33475.

*Primary Examiner*—Jean C. Witz
*Assistant Examiner*—Susan Hanley
*Attorney, Agent, or Firm*—Nikaido Marmelstein Murray & Oram, LLP

[57] ABSTRACT

A process for producing N-acetylglucosamine-6-phosphate deacetylase comprising incubating a microorganism which belongs to the marine psychrotrophic bacterium Vibrio sp. and recovering the N-acetylglucosamine-6-phosphate deacetylase from the culture thus obtained; N-acetylglucosamine-6-phosphate deacetylase; and a bacterium belonging to the marine psychrotrophic bacterium Vibrio sp.

7 Claims, 1 Drawing Sheet

PROCESS FOR PRODUCING N-ACETYLGLUCOSAMINE-6-PHOSPHATE DEACETYLASE

BACKGROUND OF THE INVENTION

This invention relates to an advantageous process for producing N-acetylglucosamine-6-phosphate deacetylase.

The enzyme obtained by the present invention, namely, N-acetylglucosamine-6-phosphate deacetylase is important in the field of biotechnology. Moreover, D-glucosamine 6-phosphate represented by the following chemical structural formula produced by this enzyme is a useful substance as a substrate in the fields of biochemistry and medicine:

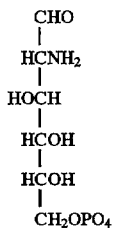

N-Acetylglucosamine-6-phosphate deacetylase is an enzyme which acts on the acetamido group of N-acetylglucosamine 6-phosphate represented by the following chemical structural formula (deacetylation) to thereby form D-glucosamine 6-phosphate. Although there has been known a method for producing this enzyme by using *Escherichia coli*, the enzyme thus obtained has only a low activity and thus is unusable industrially:

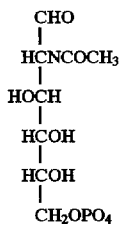

SUMMARY OF THE INVENTION

The present inventors have conducted repeated studies on a microorganism which belongs to the marine psychrotrophic bacterium Vibrio sp. As a result, they have successfully found out that this microorganism produces a large amount of an enzyme capable of deacetylating N-acetyl-D-glucosamine 6-phosphate, thus completing the present invention.

Accordingly, an object of the present invention is to provide a process whereby N-acetylglucosamine-6-phosphate deacetylase can be produced industrially advantageously.

To achieve this object, the process for producing N-acetylglucosamine-6-phosphate deacetylase of the present invention comprises incubating a microorganism (strain) which belongs to the marine psychrotrophic bacterium Vibrio sp. and is capable of producing N-acetylglucosamine-6-phosphate deacetylase and recovering (isolating) N-acetylglucosamine-6-phosphate deacetylase from the culture thus obtained.

DESCRIPTION OF THE PREFERRED EMBODIMENTS

Figure 1:
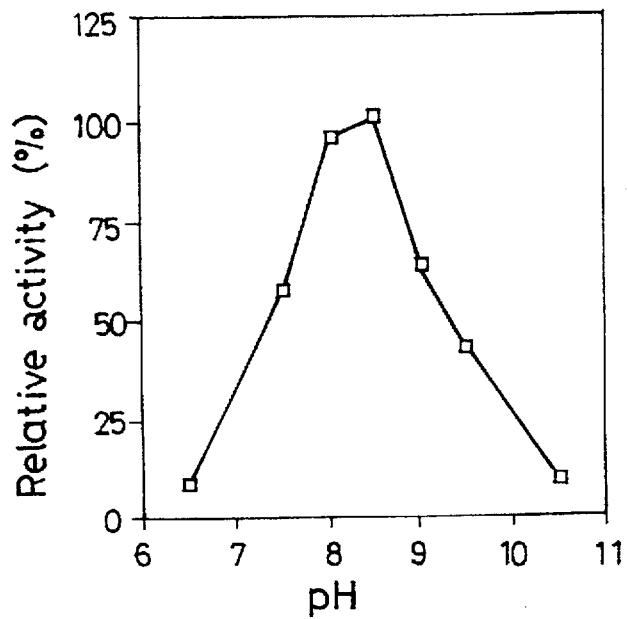
FIG. 1 shows the relationship between the relative activity (%) of N-acetylglucosamine-6 -phosphate deacetylase obtained by the present invention and the pH value.

The microorganism producing N-acetylglucosamine-6-phosphate deacetylase to be used in the present invention is one which belongs to the marine psychrotrophic bacterium Vibrio sp. and has, for example, the following mycological properties. Any microorganism may be used therefor, so long as it belongs to the low temperature bacteria of the genus Vibrio and is capable of producing N-acetylglucosamine-6-phosphate deacetylase. For example, use can be made of a marine low temperature bacterium P2K-5 strain (FERM BP-5769) isolated from the deep sea of the area of the Japan Trough by the present inventors. The marine low temperature bacterium P2K-5 strain was deposited, on the basis of Budapest Treaty, with National Institute of Bioscience and Human-Technology, Agency of Industrial Science and Technology, residing at 1-3, Higashi 1 chome, Tsukuba-shi, Ibaraki-ken 305 Japan, under the accession number FERM BP-5769, on the day of Dec. 10, 1996.

The mycological properties of this marine low temperature bacterium P2K-5 strain (FERM BP-5769) are as follows.

1. Morphological property
   (1) Cell morphology rod.
   (2) Flagella morphology : polar flagellation.
   (3) Gram stain : negative.
2. Physiological property
   (1) Growth temperature at
       4° C. : +.
       25° C. : +.
       30° C. : +.
   (2) 0-F test : fermentative.
   (3) Requirement for salt: +.
   (4) Chromogen : −.
   (5) Oxidase : +.
   (6) Catalase : +.
3. Origin seawater in the area of the area of the Japan Trough (depth: 6,000 m).

These mycological properties are examined in accordance mainly with Yoshio Ezura, "Engan Kankyo Chosa Manyuaru II [Suishitsu Biseibutsu-hen]", ed. by Nippon Kaiyo Gakkai, Koseisha Koseikaku, pp. 357–364 (1990). Also, use is made of Kazoo Komagata, "Biseibutsu no Bunrui to Dotei (II)", (revised, ed. by Takeharu Hasegawa), Gakkai Shuppan Senta, pp. 99–161 (1985) as a reference.

Based on Ezura and Shimizu, "Kaiyo Saikin no Kan-i Dotei Zushiki (Engan Kankyo Chosa Manyuaru II) [Suishitsu Biseibutsuhen]", ed. by Nippon Kaiyo Gakkai, Koseisha Koseikaku, pp. 357–364 (1990), the above-mentioned mycological properties are compared with the data given in Bergey's Manual of Systematic Bacteriology, vol. 1 (ed. by N.R. Krieg and J.G. Holt, Williams & Wilkins, Baltimor, 1984) and Bergey's Manual of Determinative Bacteriology (9th ed., ed. by J.G. Holt, N.R. Krieg, P.H.A. Sneath, J.T. Staley and S.T. Williams, Williams & Wilkins, Baltimor, 1984). As a result, this marine low temperature bacterium P2K-5 strain (FERM BP-5769) is identified with a bacterium belonging to the marine psychrotrophic bacterium Vibrio sp.

With the use of this marine low temperature bacterium P2K-5 strain (FERM BP-5769), N-acetylglucosamine-6- phosphate deacetylase can be produced by inoculating this strain into an appropriate medium and incubating the same by a conventional method preferably in the presence of an inducer. As the inducer, use can be made of chitin, decomposition products of chitin, N-acetylglucosamine 6-phosphate, N-acetylglucosamine or N-acetylglucosamine oligomers either alone or as a combination of two or more thereof. Preferable examples of the inducer include N-acetylglucosamine and N-acetylglucosamine oligomers. It is the most desirable to use N-acetylglucosamine as the inducer. The inducer is added to give a concentration of at least 0.1 g/l, preferably 1.0 to 50 g/l. As the medium, any commonly employed one may be used without specific restriction. For example, use can be made of glucose, maltose, xylose, sucrose, peptone, etc. as the carbon source. As the nitrogen source, use can be made of organonitrogen materials such as yeast extract, peptone, meat extract and amino acid solutions and inorganic nitrogen compounds such as ammonium sulfate and ammonium chloride. It is also possible to use the inducer as the carbon source or the nitrogen source. As the inorganic salts, use cam be made of magnesium sulfate, magnesium chloride, sodium phosphate, potassium phosphate, potassium chloride, sodium chloride, calcium chloride, etc. appropriately combined with each other. The pH value of the above-mentioned medium is regulated within a range of from 6.5 to 8.5. The medium is sterilized in an autoclave. The incubation is effected at a temperature ranging from 4 to 35° C., preferably from 15 to 28° C., for 20 to 48 hours under aeration/stirring or shaking. By using a plate medium containing the above-mentioned carbon source, nitrogen source, inorganic salts and agar, the incubation is effected at a temperature of from 4 to 35° C., preferably from 15 to 28° C., for 20 to 72 hours. Alternatively, this strain can be incubated statically.

From the culture thus obtained, the medium may be separated from the cells by a method commonly employed in the art such as centrifugation or filtration. Centrifugation is appropriately employed therefor. The enzyme accumulated in the cells may be extracted by a method commonly employed in the art, for example, ultrasonic cell disruption, cell disruption with the use of a Dynomill cell disrupter wherein the culture is rotated together with glass beads, or destruction of cell membrane with the use of enzymes such as lysozyme or organic solvents such as toluene. The enzyme can be recovered by extracting the cells with the use of an appropriate method selected from among those described above.

The N-acetylglucosamine-6-phosphate deacetylase may be further purified, if necessary, from the crude enzyme solution thus extracted by appropriately combining means commonly employed for purifying enzymes, for example, ammonium sulfate precipitation, ion exchange chromatography, gel filtration, adsorption chromatography, reversed phase chromatography, hydrophobic chromatography and preparative electrophoresis.

The N-acetylglucosamine-6-phosphate deacetylase obtained by the process of the present invention has the following physicochemical properties.

(1) Action: acting on the acetamido group of N-acetylglucosamine 6-phosphate (deacetylation) to thereby form glucosamine 6-phosphate.

(2) Optimum pH value: 8.0 – 9.0 (as shown in FIG. 1, the relative activity attains a high level at pH 8.0 to 9.0).

(3) Stable pH value: 8.0 – 10 (after incubating at 20° C. for 30 minutes, at least 90% of the activity is sustained).

Figure 2:
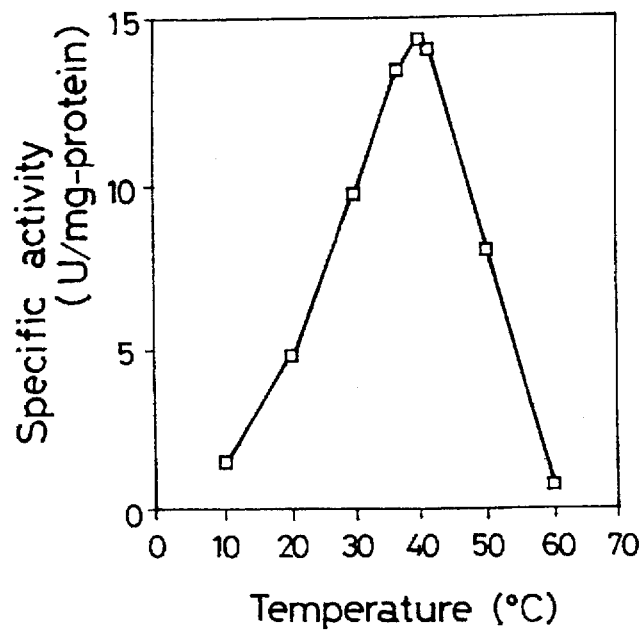
FIG. 2 shows the relationship between the specific activity (U/mg-protein) of N-acetylglucosamine-6 -phosphate deacetylase obtained by the present invention and the temperature (° C.).

(4) Optimum temperature: 40 –42° C. (as shown in FIG. 2, the specific activity (U/mg-protein) attains a high level at a temperature of from 40 to 42° C.). Activity is observed within a temperature range of from 5 to 60° C.

(5) Heat stability: after incubating at a temperature up to 30° C. at pH 8.5 for 30 minutes, 100% of the activity is sustained. After incubating at a temperature up to 40°C. at pH 8.5 for 30 minutes, at least 60% of the activity is sustained.

The activity is determined by the following method. Namely, 0.1 ml of a 1% solution of N-acetylglucosamine-6-phosphate is added as a substrate to 0.3 ml of a 75 mM phosphate buffer solution (pH 8.5). Next, 0.1 ml of an enzyme solution is further added thereto followed by incubation at 40° C. for 30 minutes. Then the D-glucosamine 6-phosphate thus formed is determined by the indole/hydrochloric acid colorimetry.

The amount of the enzyme by which 1 μmol of the amino sugar is formed in a minute is referred to as 1 U (unit).

To further illustrate the present invention in greater detail, the following Examples will be given.

Example 1

A commercially available plate medium BHI (trade name, mfd. by DIFCO) containing 3 g of agar was inoculated with the marine psychrotrophic bacterium Vibrio sp. (Vibrio sp. P2K-5, FERM BP-5769), which was then incubated therein at 20°C. for 36 hours. Next, the cells were collected with a sterilized spatula and inoculated into a liquid medium as shown below. After mixing, the cells were incubated at 20° C. for 26 hours while shaking under aerobic conditions.

Medium: containing, per 800 ml of the medium, 2.4 g of ammonium nitrate, 0.8 g of dipotassium hydrogenphosphate, 8 g of sodium chloride, 0.4 g of magnesium sulfate, 0.8 g of calcium chloride and 40 g of N-acetylglucosamine as the inducer for the enzyme.

(1) Purification step 1

Then the culture was centrifuged at 8,000 × g for 20 minutes to thereby give 21 g of wet cells. The obtained cells were suspended in 40 ml of physiological saline. After effecting ultrasonication at 0° C. for 10 minutes (each cycle consisting of the operation for 20 seconds and rest for 20 seconds), the suspension was centrifuged at 12,000 × g for 1 hour to thereby give the supernatant. The total activity and specific activity of the enzyme contained in the supernatant were respectively 150 U and 0.188 U/mg-protein based on the N-acetylglucosamine 6-phosphate.

(2) Purification step 2

The supernatant obtained in the above purification step 1 was passed through 30 ml of a DEAE Bio-Gel A (trade name, mfd. by Bio-Rad) column preliminarily equilibrated with a 10 mM phosphate buffer solution (pH 7.0) and thus the target enzyme was adsorbed thereby. After washing with the same phosphate buffer solution, the column was eluted while changing the concentration of sodium chloride stepwise to thereby give a fraction of the target enzyme having a total activity of 102 U and a specific activity of 0.657 U/mg-protein based on N-acetylglucosamine 6-phosphate.

(3) Purification step 3

The active fraction as described above was further passed through a 10 mM Hydroxyapatite (trade name, mfd. by Toagosei Chemical Industry Co., Ltd.) column preliminarily equilibrated with a 10 mM phosphate buffer solution (pH 7.0) and thus the target enzyme was adsorbed thereby. After washing with the same phosphate buffer solution, the column was eluted while changing the concentration of the phosphate buffer solution stepwise to thereby give a preparation of the target enzyme having a total activity of 21.2 U and a specific activity of 2.30 U/mg-protein based on N-acetylglucosamine 6-phosphate.

(4) Purification step 4

Next, the active fraction obtained in the above purification step 3 was passed through a HiTrap™Q (trade name, mfd. by Pharmacia) column preliminarily equilibrated with a 100 mM potassium dihydrogenphosphate solution and thus the target enzyme was adsorbed thereby. After washing with the same solution of potassium dihydrogenphosphate, the column was eluted while changing the concentration of the sodium chloride stepwise to thereby give a preparation of the target enzyme having a total activity of 10.4 U and a specific activity of 1.6 U/mg-protein based on N-acetylglucosamine 6-phosphate.

(5) Purification step 5

The active fraction obtained in the above purification step 4 was passed through 2 ml of a QAE Sephadex A-50 (trade name, mfd. by Pharmacia) column preliminarily equilibrated with a 10 mM phosphate buffer solution (pH 7.0) and thus the target enzyme was adsorbed thereby. After washing with the same phosphate buffer solution, the column was eluted while changing the concentration of the sodium chloride stepwise to thereby give a preparation of the target enzyme having a total activity of 3.58 U and a specific activity of 9.65 U/mg-protein based on N-acetylglucosamine 6-phosphate.

When electrophoresed on an SDS polyacrylamide gel, this enzyme preparation showed a single band which proved that it was homogeneous as a protein.

This enzyme exerted no action on N-acetylgalactosamine.

Example 2

Determination was made on the total and specific activities of the deacetylase action on N-acetyl-glucosamine of the enzymes obtained in the above purification steps 1 to 3. Table 1 shows the results.

TABLE 1

| Enzyme | Total activity (U) | Specific activity (U/mg-protein) |
|---|---|---|
| purification step 1 | 75 | 0.094 |
| purification step 2 | 50 | 0.313 |
| purification step 3 | 12 | 0.92 |

Although the enzyme of the present invention shows a deacetylase action on N-acetylglucosamine too as described above, this action is weaker than the one observed when N-acetylglucosamine-6-phosphate is employed as the substrate.

The N-acetylglucosamine-6-phosphate deacetylase of the present invention shows its activity of 9.65, 14.5 and 7.5 U/mg-protein respectively at 30, 40 and 50° C. That is to say, the N-acetylglucosamine-6-phosphate deacetylase of the present invention not only has an extremely high activity but also sustains a high activity at a temperature of 40° C. or higher, which brings about an advantage that it requires in use no cooling apparatus. The present invention further provides a technique whereby N-acetylglucosamine-6-phosphate deacetylase can be industrially produced usually at room temperature without heating, thus costing less.

What is claimed is:

1. A process for producing N-acetylglucosamine-6-phosphate deacetylase comprising incubating a microorganism which is the marine low temperature bacterium P2K-5 strain (Vibrio sp. P2K-5 strain. FERM BP-5769) to produce N-acetylglucosamine-6-phosphate deacetylase and recovering N-acetylglucosamine-6-phosphate deacetylase from the culture thus obtained.

2. A process for producing N-acetylglucosamine-6-phosphate deacetylase as set forth in claim 1 wherein said N-acetylglucosamine-6-phosphate deacetylase has an activity within a temperature range of from 5 to 60° C.

3. A process for producing N-acetylglucosamine-6-phosphate deacetylase as set forth in claim 1 wherein said N-acetylglucosamine-6-phosphate deacetylase has an optimum temperature of from 40 to 42° C.

4. A process for producing N-acetylglucosamine-6-phosphate deacetylase as set forth in claim 1 wherein said N-acetylglucosamine-6-phosphate deacetylase sustains 100% of its activity after incubating at temperatures up to 30° C. at pH 8.5 for 30 minutes.

5. A process for producing N-acetylglucosamine-6-phosphate deacetylase as set forth in claim 1 wherein said N-acetylglucosamine-6-phosphate deacetylase sustains at least 60% of its activity after incubating at temperatures up to 40° C. at pH 8.5 for 30 minutes.

6. An isolated bacterium belonging to the low temperature bacterium P2K-5 strain (Vibrio sp. P2K-5 strain, FERM BP-5769).

7. The bacterium of claim 6 wherein said bacterium, if incubated, produces N-acetylglucosamine-6-phosphate deacetylase.

* * * * *